(12) United States Patent
Hirschenbain et al.

(10) Patent No.: US 8,804,904 B2
(45) Date of Patent: Aug. 12, 2014

(54) CT PERFUSION PHANTOM

(71) Applicants: Aviv Hirschenbain, Raanana (IL); Jacob Sosna, Rishon Lezion (IL)

(72) Inventors: Aviv Hirschenbain, Raanana (IL); Jacob Sosna, Rishon Lezion (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 14/139,894

(22) Filed: Dec. 24, 2013

(65) Prior Publication Data

US 2014/0114176 A1 Apr. 24, 2014

Related U.S. Application Data

(63) Continuation of application No. 13/147,378, filed as application No. PCT/IB2010/050475 on Feb. 3, 2010, now Pat. No. 8,636,411.

(60) Provisional application No. 61/149,371, filed on Feb. 3, 2009.

(51) Int. Cl.
*G01N 23/04* (2006.01)
*A61B 6/00* (2006.01)

(52) U.S. Cl.
CPC ................................ *A61B 6/504* (2013.01)
USPC ........................................................ 378/62

(58) Field of Classification Search
CPC ...... A61B 6/0206; A61B 6/482; A61B 6/484; G01N 23/04
USPC .............................................. 378/4, 19, 62, 63
See application file for complete search history.

(56) References Cited

U.S. PATENT DOCUMENTS 7,627,078 B2 * 12/2009 Hsieh et al. ....................... 378/4
8,068,665 B2 * 11/2011 Ohishi ............................. 382/154
8,285,014 B2 * 10/2012 Lauritsch et al. .............. 382/128

* cited by examiner

*Primary Examiner* — Irakli Kiknadze
(74) *Attorney, Agent, or Firm* — Mark M. Friedman

(57) ABSTRACT

A physical phantom reference to control for variability of computed tomography measurement results duplicates the density curve of blood perfusion of contrast material in a healthy aorta or large artery to normalize observed changes in healthy arterial blood perfusion when calculating the reduction in tumor blood perfusion between two examination times. In one embodiment, a plurality of compartments with different concentrations of contrast material corresponding to a density curve of blood perfusion of a healthy tissue are positioned-in a screening field of a CT machine so the CT machine images the compartments when it images the healthy tissue. In another embodiment, a pipe containing fluid receives an injection of contrast material from the injector when the injector injects the contrast material into the patient, the pipe having sections of varying diameter so the sections together correspond to a blood perfusion curve of the contrast material in a healthy tissue.

22 Claims, 6 Drawing Sheets

CT PERFUSION PHANTOM

FIELD AND BACKGROUND OF THE INVENTION

The present invention relates to improving therapy and drug tailoring in oncology patients, and, more particularly to improving the reliability of computed tomography ("CT") examinations measuring the effectiveness of the drug treatment in reducing cancerous tissue.

More than 15 million follow-up examinations are performed annually to monitor cancer treatment in the West. The main imaging modalities are CT, MRI and PET/CT. MRIs and PET/CT are the most sensitive in detection but have drawbacks regarding their large scale use for the millions affected. These drawbacks include (i) a limited number of equipment (ii) long and uncomfortable examination time and (iii) very expensive to use. CT machines, although less sensitive for functional changes, have the advantage of being relatively cost-effective, not complicated, requiring only short examination time and there are a large number of available scanners.

Conventional CT blood perfusion studies employ CT examinations on two different dates (the first date being before the drug treatment was initiated) and calculate a rate of reduction in blood perfusion between the two dates. Since cancerous cells have a much higher blood supply, called neovascularization, they are assumed to have a proportionately higher rate of blood perfusion.

The blood perfusion measured by CT scanners has severe reliability problems. Blood perfusion may be measured by detecting presence of contrast material pixel by pixel as the contrast material, such as iodine, flows through the cancerous tissue. FIG. 1 is a perfusion curve showing a combination of two curves, (i) wash-in of blood containing contrast material increasing exponentially and (ii) wash-out of this blood containing contrast material decreasing logarithmically. As is known, the actual perfusion, C, the maximum attenuation point may be very sensitive to changes in A and B and this makes it a good measure to represent changes in overall perfusion in the tissue. Techniques for calculating perfusion include the deconvolusion technique and the maximal slope technique. However, the variables obtained with either technique may be influenced by external and internal factors not reflecting changes in the true tissue perfusion rate. Accordingly, when the perfusion rate may be re-measured at the second CT examination, factors that are unrelated to the true tissue perfusion and hence also unrelated to the value of the drug or treatment, distort the comparison of blood perfusion values required to perform drug tailoring.

The factors influencing the maximum attenuation point include external factors such as injection rate, contract dose and concentration, machine calibration, stability of the x-ray tube, and more. GE, Phillips, Toshiba and Siemens make most of the CT machines sold today. Each of these different manufacturers employs different algorithms and methods to calculate the blood perfusion result from the imaging data obtained during the CT examination. Since the second CT examination may be performed by a different machine, the results will be unreliable.

Internal factors also contribute to variability of CT exam blood perfusion readings. During the first examination, the patient's heart rate may have been 60 and during the second examination the same patient's heart rate may have been 70. Similarly, the patient may have been dehydrated during only one of the examinations. Both of these facts affect blood perfusion results. Other internal factors may include aortic insufficiency, cardiac output variability, the patient's general metabolic status and other patient related changes. In addition, a 6% change in the calibration of HU of water may be observed even within a period of minutes.

One way that the prior art CT examinations have attempted to deal with the variability that distorts the results of CT examinations and limits their reliability and usefulness in drug tailoring is by using a control tissue, such as a healthy aorta, that represents the input function of blood. The idea is to scan the healthy aorta at the same time that the cancerous tissue is scanned using the same CT equipment. An underlying assumption is made that blood perfusion in the cancerous tissue, for example in the kidney, will not change from the first examination to the second if no changes were observed in the actual tumorous tissue.

In practice, however, this underlying assumption is incorrect. In fact, there are daily changes in cardiac output, which may cause daily changes in the mathematical relationship (i.e. ratio) between blood perfusion in the cancerous tissue (i.e. liver) and blood perfusion in the healthy tissue (i.e. heart). Accordingly, conventional CT imaging is left with the unreliability caused by the variability associated with the above internal and external factors. Because of the known unreliability, a significant reduction in blood perfusion may be typically required before judging that a drug treatment is effective for a certain patient because it is assumed that some of the observed apparent decrease in blood perfusion of the cancerous tissue may in fact have been caused by factors unrelated to true changes in tissue perfusion. This limits the usefulness of CT examinations in drug tailoring and harms patient outcomes.

There is a compelling need to have an apparatus or method that will significantly improve oncology treatment outcomes, such as by significantly improving the reliability of CT scanners and improve drug tailoring.

SUMMARY OF THE PRESENT INVENTION

One aspect of the present invention is directed to an apparatus useful for computed tomography imaging, comprising a phantom control reference, comprising a plurality of compartments, each compartment containing contrast material, the contrast material differing in density from one compartment to another throughout the plurality of compartments, the densities of the contrast material in the plurality of compartments forming a series of densities that corresponds to a density curve of blood perfusion of a healthy tissue; and a controller for positioning the compartments in a screening field of view of a CT machine so the CT machine can take a series of images of the compartments at a same examination time that the CT machine takes a series of CT images of the healthy tissue.

A further aspect of the present invention is directed to an apparatus useful for computed tomography imaging, comprising a phantom control reference comprising a pipe containing a fluid and capable of receiving an injection of the contrast material from an injector at a time that the injector injects the contrast material into a patient, the pipe having sections of varying diameter, the sections of known flow rate so that a varying density of contrast material throughout the sections of the pipe correspond to a blood perfusion curve of the contrast material in a healthy tissue of the patient as measured during a computed tomography examination.

A still further aspect of the present invention is directed to a method of using computed tomography equipment to measure blood perfusion in a patient having a cancerous tissue, comprising measuring a blood perfusion of contrast material in the cancerous tissue and in healthy tissue in the patient at a first examination time using a particular piece of computed tomography equipment to obtain a first cancer/healthy perfusion ratio result; measuring a blood perfusion of the contrast material in a healthy tissue phantom at the first examination time using the particular piece of computed tomography equipment, the healthy tissue phantom having a known density curve selected to correspond to the blood perfusion of the healthy tissue to obtain a first phantom perfusion result; re-measuring a blood perfusion of the contrast material in the cancerous tissue and in the healthy tissue in the patient at a second examination time, using a second piece of computed tomography equipment, to obtain a second cancer/healthy perfusion ratio result; and re-measuring a blood perfusion of the contrast material in the healthy tissue phantom at the second examination time using the second piece of computed tomography equipment to obtain a second phantom perfusion result.

A still further aspect of the present invention is directed to a method of controlling for variability in measurements of healthy tissue blood perfusion for computed tomography imaging, comprising using a particular piece of computed tomography equipment, measuring at a first time a blood perfusion of contrast material in a healthy aorta in a patient while measuring a blood perfusion of the contrast material in a healthy tissue phantom having a known density curve selected to correspond to the blood perfusion of the healthy aorta to obtain a first phantom perfusion result; repeating the measurements at a later time for the patient using a second piece of computed tomography equipment; and normalizing the results of the measurement of the blood perfusion in the healthy tissue found using the second piece of computed tomography equipment by using a change, if any, between the first phantom perfusion result and the second phantom perfusion result.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

Figure 1:
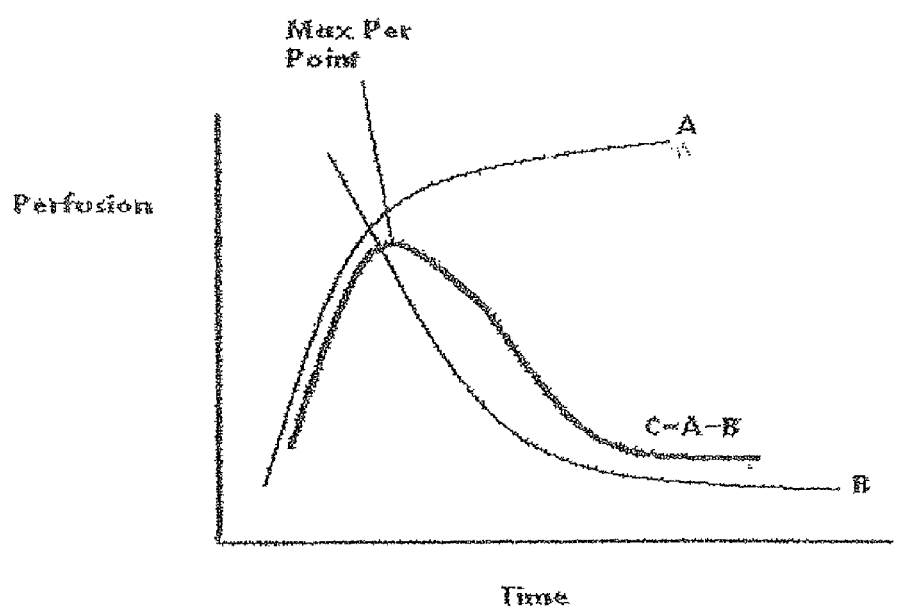
FIG. 1 is a graph of blood perfusion showing Pmax and a slope from base to peak enhancement.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides more reliable blood perfusion measurements in computed tomography that may typically be used for drug tailoring in the early stages of cancer. At the same time that a CT machine takes images of contrast material of a cancerous tissue and in healthy issue of a patient to calculate blood perfusion in the healthy and cancerous tissues, an apparatus representing a phantom control reference may be positioned in the field of view of the CT machine. In one embodiment, the apparatus may comprise compartments containing contrast material in differing densities that may cumulatively correspond to a density curve of blood perfusion of the healthy tissue. A controller positions the compartments so the CT machine can scan them at a same examination time that the CT machine takes a series of CT images of the healthy tissue. In another embodiment, a phantom control reference may comprise a pipe having water that can receive an injection of the contrast material from an injector at the same time the injector injects the contrast material into a patient. Since the pipe may have sections of varying diameter and of known flow rate, the varying density of contrast material throughout the sections of the pipe may correspond to a blood perfusion curve of the contrast material in a healthy tissue of the patient as measured during a CT examination. Using a particular piece of computed tomography equipment, we measure blood perfusion in a healthy aorta while measuring blood perfusion in the healthy tissue phantom having a known density curve. After repeating the measurements at a later time using a second piece of computed tomography equipment we normalize the results of the measurement of the blood perfusion in the healthy tissue phantom by comparing its change to the change between the first phantom perfusion result with the second phantom perfusion result. Drugs may be tailored to the individual patient based on changes in blood perfusion and changes in tumor reduction in matter days in some cases.

In contrast to the prior art, in which CT machines provide unstable and unreliable blood perfusion results to be compared at different times, the method and apparatus of the present invention may provide a significantly more stable and accurate measurement of blood perfusion using CT machines. In further contrast to the prior art, in which conventional CT imaging cannot resolve small but meaningful blood flow aberrations in early stages of cancer, the CT method and apparatus of the present invention may be able to do so. In still further contrast to prior art conventional CT imaging, in which changes indicating effectiveness of a drug can be observed in weeks or months, the CT method and apparatus of the present invention may allow observation of changes in days. In further contrast to the prior art, in which the unreliability of CT blood perfusion results may require a significant reduction in blood perfusion results (in some cases, for example, 50%) before concluding that a therapy is effective in reducing the tumor, the method and apparatus of the present invention may allow a conclusion of effectiveness of a drug after only a much smaller reduction in blood perfusion is found (in some cases, for example, 20%, 25% or 30%) because the results may be more reliable. In further contrast to the prior art, in which CT exams for measuring blood perfusion are rendered less reliable by use of different CT machines made by different manufacturers between a first and a second measurement, the method and apparatus of the present invention may allow use of any CT machine available without having to be concerned that variations in machine manufacturers will interfere with the reliability of results. In still further contrast to the prior art, in which drug tailoring to find the right drug for a given individual can take many months, during which time the patient may die, the time needed to perform drug tailoring using blood perfusion tests of the present invention may be considerably shorter. This is because each individual drug may be tested for effectiveness much quicker using the present invention than the prior art. Unlike the prior art, where it may take weeks to months to test the effectiveness of a single cancer drug treatment because lymph node tumor shrinkage occurs well after changes in blood perfusion yet blood perfusion results are unreliable, the blood perfusion results of the present invention may be reliable. In contrast to the prior art, in which attempts to control for variability in blood perfusion results by using a control test of a healthy aorta are ineffective since changes in cardiac output between studies may cause significant variability in results, the present invention may successfully control for variability of results pertaining to external factors such as injection rate, contract dose, concentration, machine calibration, stability of the X-ray tube, and internal factors such as size and condition of the IV, changes in heart rate and cardiac output. In still further contrast of the prior art, in which the number of slides needed in a CT examination in order to be able to calculate blood perfusion may be approximately 12, which exposes the patient to radiation during that time, using the present invention the number of slides may be reduced (e.g. to 6) and the length of exposure to potentially harmful radiation may also be reduced. By measuring the value of the phantom control reference, the number of exposures in later examinations may be curtailed since the reproducibility of the perfusion curves may be improved.

The principles and operation of a method and system for interactive electronic detection, enforcement and education according to the present invention may be better understood with reference to the drawings and the accompanying description.

The term "computed tomography imaging" means imaging using computed tomography.

A phantom control reference 10, in its most general sense, may be anything that may contain contrast material of known densities corresponding to a density curve of blood perfusion of the healthy tissue of a patient that can be scanned in the field of view of a computed tomography (CT) machine while the patient's healthy tissue is also being scanned, and as to which an output can be obtained from the CT machine representing a density curve of blood perfusion for the phantom control reference. Phantom control reference 10 may be external to the patient's body. At around the same time an output may be obtained for the phantom control reference, the CT machine may provide an output for the blood perfusion of the healthy tissue and for the cancerous tissue of the patient.

One way of constructing a phantom control reference is to have comprise a plurality of compartments 20, each compartment 20A, 20B, 20C, 20D, 20E, 20F, 20G, 20H, 20I, 20J, 20K, 20L may contain contrast material differing in density from one compartment to another throughout the plurality of compartments. The densities of the contrast material in the plurality of compartments are known densities, and together they may form a series of densities that corresponds to a density curve of blood perfusion of a healthy tissue as measured by a CT machine. The number of compartments in the plurality may match the number of slices of CT images taken of the healthy tissue. A controller would be used to position the compartments in a screening field of view of the CT machine so the CT machine can take a series of images of the compartments at a same examination time that the CT machine takes a series of CT images of the healthy tissue. More particularly, the controller may repeatedly and automatically position the compartments in a pre-defined spatial relationship.

Figure 2:
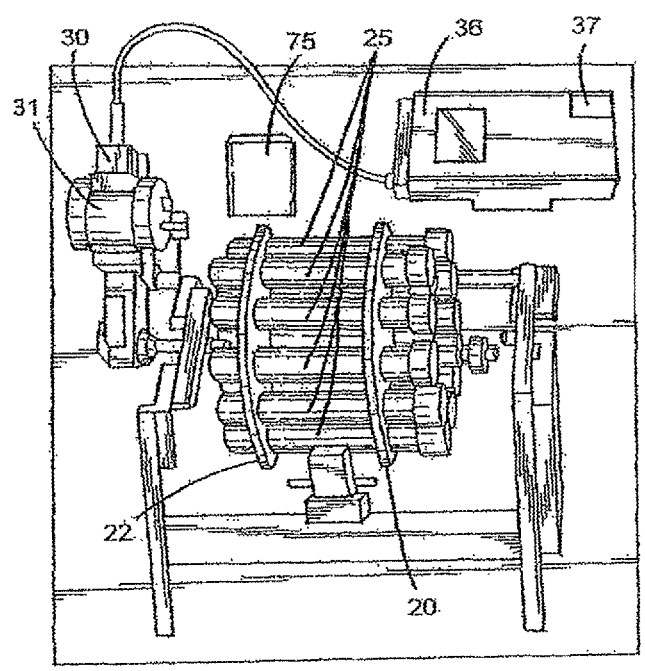
FIG. 2 is a photo of an apparatus comprising a phantom control reference, in accordance with one embodiment of the present invention.

In accordance with one embodiment shown in FIG. 2, one way of constructing the apparatus comprising a phantom control reference 10 is to have a wheel 20 that may have a series of test tubes 25 on a periphery 22 of wheel 20. The test tubes contain known varying densities of a contrast material in a fluid such as water or another low density fluid. The series of densities of the contrast material in the series of test tubes may form a density curve corresponding to a density curve measuring blood perfusion of a healthy tissue, as measured by a CT machine.

As seen in FIG. 2, test tube wheel 20 sitting on a CT table may be consecutively rotated by a motor 30, motor 30 operatively engaged to a gearbox 31, so that each test tube 25 in the series of test tubes 25 on wheel 20 is successively positioned into a field of view of the CT imaging scan of a CT machine while the same CT machine is scanning various slices of the patient's healthy tissue. A controller 36 may direct motor 30 to rotate at speed so as to synchronize its rotation and positioning of test tubes 25 with the series of scans taken by the same CT machine of the patient's healthy tissue. Reduction gear box 31 may reduce motor speed. A reduction gearbox output may actually drive the test tube wheel 20. The perfusion phantom robot may set the position of test tubes 25 according to a predefined program so that imaging results of test tubes 25 may be aggregated to form coordinates of a density curve as directed by software. Apparatus 10 may be constructed so as to contain X-ray attenuation materials in order to reduce image artifacts and to achieve densities that are seen in clinical imaging. Alternatively, the test tube wheel 20 may be held stationary and software 37 within controller 36 may be used to direct the CT machine to image successive test tubes within the wheel at a series of time intervals.

FIG. 2 also shows an X-ray detector 75 whose purpose is to ensure that the movement of the phantom control reference 10 will occur at times when there is no influx of photons to the detector.

In any of the embodiments, the phantom reference control may be selected to result in a known density and a known series of densities. Notwithstanding this, the actual measured perfusion result of the healthy tissue phantom may vary from examination to examination due to external factors such as differences in CT machines, the different logarithms used by different brands of CT machines and the difference performances of different CT machines on different days.

Furthermore, the selection of what the density curve of the healthy tissue phantom should be may be targeted to falling within the range of density curves of healthy tissue from experience of practitioners in the field. Alternatively, the perfusion may be based on a previously measured blood perfusion of the specific healthy tissue of the specific patient being examined. It is noted that a common example of the healthy tissue is a healthy aorta.

Figure 3:
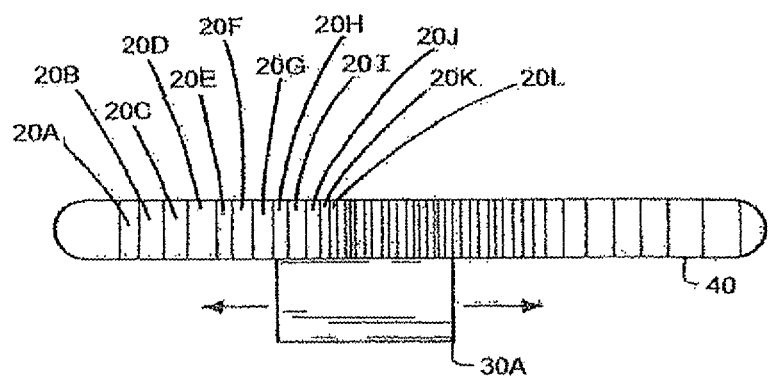
FIG. 3 is a front view of a tube in a phantom control reference, in accordance with one embodiment of the present invention.

In accordance with FIG. 3, the compartments 20 may be separate sections 20A, 20B, 20C, 20D, 20E, 20F, 20G, 20H, 20I, 20J, 20K, 20L, for example vertical sections, of a movable tube 40. The tube 40 may be moved through the screening field of view of the CT machine by a controller 30A that may direct a motor 30A to linearly move tube 40 so as to synchronize positioning of sections 20A-20L with the series of scans taken by the same CT machine of the patient's healthy tissue.

Figure 4:
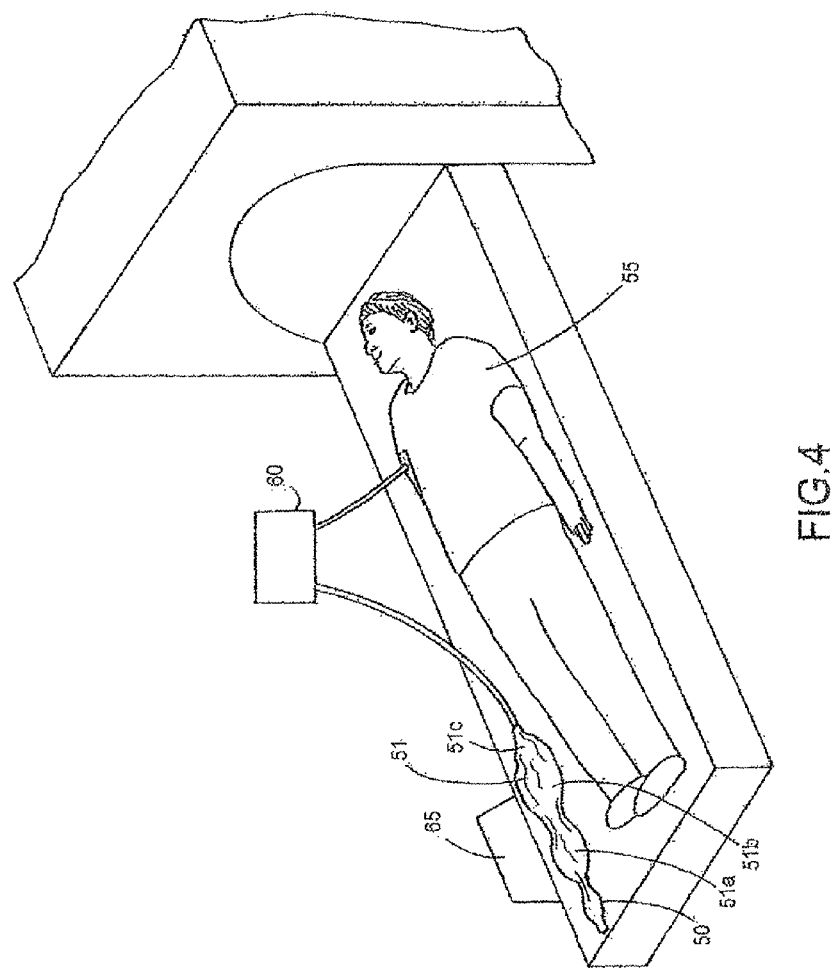
FIG. 4 is plan view of a phantom control reference in accordance with a further embodiment of the present invention.

Rather than simulate density, the phantom control reference may also directly simulate flow rate, for example the flow rate of the contrast material or the flow rate of the liquid containing the contrast material. FIG. 4 shows a phantom control reference that may comprise a pipe 50 containing a fluid 51. Pipe 50 may be capable of receiving an injection of the contrast material (for example in a saline solution) from an injector 60 at the same time that injector 60 may inject the contrast material into a patient 55. Pipe 50 may have sections 51a, 51b, 51c, etc., of varying diameter so that each of the sections has a known flow rate. Accordingly, the series of varying densities of contrast material throughout the sections of pipe 50 may form a density curve that may correspond to a blood perfusion curve of the contrast material in a healthy tissue of the patient as measured during a computed tomography examination. The number of sections in pipe 50 may correspond to the number of computed tomography images taken of the healthy tissue during a computed tomography examination.

It is noted that the phantom control reference of FIG. 4 may also be suitable for use in MRI imaging in a manner similar to that described herein with respect to CT imaging.

In any embodiment of the present invention, an output structure 65 connected to the CT machine may provide a numerical blood perfusion result for the computed tomography images of the phantom control reference. The output structure 65 may function like the output of a regular CT machine in providing blood perfusion results.

Figure 5:
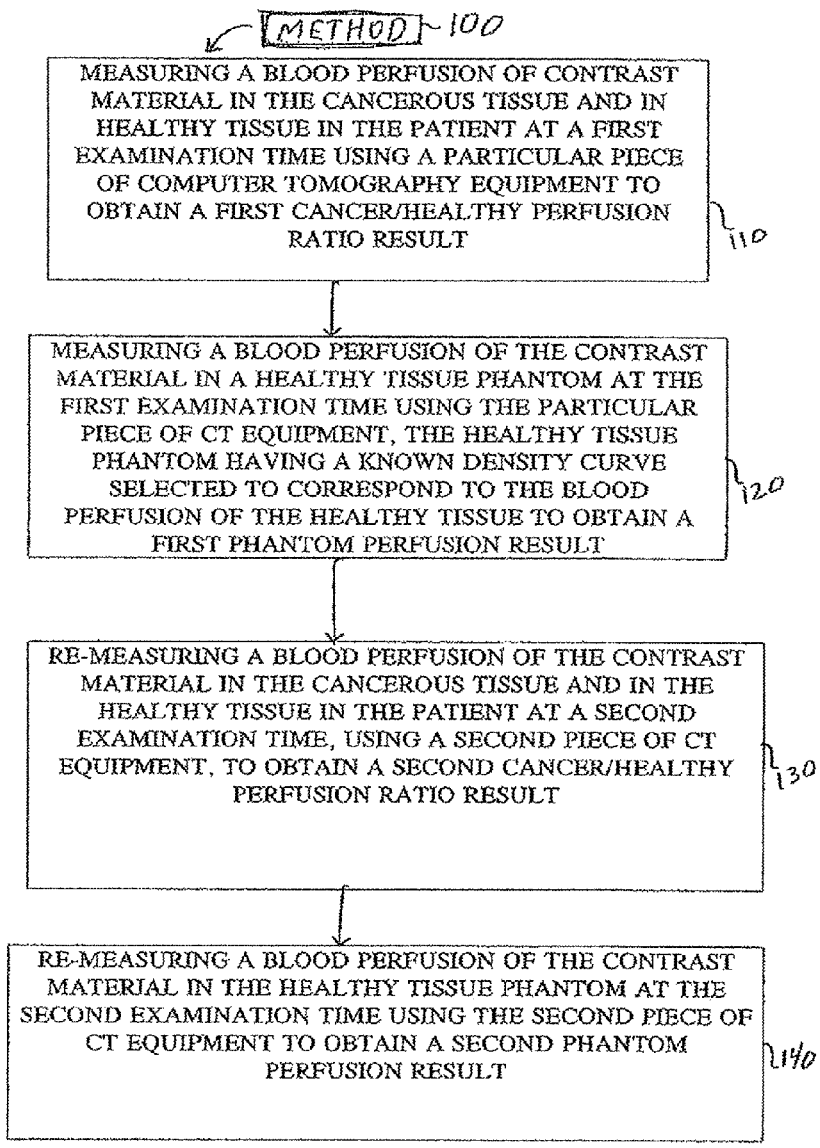
FIG. 5 is a flow chart showing a method in accordance with one embodiment of the present invention.

The present invention may also be expressed as a method, for example a method of using computed tomography equipment to measure blood perfusion in a patient having a cancerous tissue. As shown in FIG. 5, method 100 may comprise a step 110 of measuring a blood perfusion of contrast material in the cancerous tissue and in healthy tissue in the patient at a first examination time using a particular piece of computed tomography equipment to obtain a first cancer/healthy perfusion ratio result. The output structure may provide the first cancer/healthy perfusion ratio result in a form commonly used for measuring blood perfusion. For example, $\Delta HU_{tissue}$ and $\Delta HU_{artery}$ may be obtained and placed into the following equation, which is one of two commonly used equations for calculating blood perfusion:

$$CBV = \Delta HU_{tissue}/\Delta HU_{artery} \cdot N$$

where CBV stands for the calculated blood volume and is equal to changes in density of the tissue over that of the artery multiplied by the number of measurements. The other commonly used equation for calculating blood perfusion is $$R(t) = 1/CBF \cdot \Gamma^{-1}\{[\Gamma C_{tissue}(t)]/[\Gamma AIF(r)]\}$$

where R(t) stands for blood perfusion calculated over time (i.e. integrated arterial time-activity curve corrected for recirculation using a gamma function fit) and is equal to 1 divided by flow as a function of arterial input function (AIF) over time.

A further step 120 of method 100 may comprise measuring a blood perfusion of the same contrast material in a healthy tissue phantom at the same first examination time using the same piece of computed tomography equipment. In this scenario, the healthy tissue phantom may be initially designed to have a known density curve that may correspond to the blood perfusion of the healthy tissue in order to obtain a first phantom perfusion result. In the phrase "correspond to the blood perfusion of the healthy tissue" used in any method of the present invention, the word "correspond" may be understood to refer to an estimate rather than an exact match. That is, it may be that the healthy tissue phantom need not be initially selected to have the same identical blood perfusion as the healthy tissue. It may be merely selected to roughly estimate the healthy tissue blood perfusion to facilitate the normalization steps described below. One way of selecting the level of blood perfusion desired for the healthy tissue phantom may be to use a prior known blood perfusion result for the same patient's known from some previous examination, although this is not required and may not be available in certain cases.

In addition, in the phrase "known density curve that may correspond to the blood perfusion of the healthy tissue" used in methods of the present invention, the words "density curve" shall be understood to refer broadly both to a density curve as well as to a blood perfusion curve that may be derived directly from a contrast material's flow rate rather than from measurement of its density.

The output structure may produce a first phantom perfusion result that may be in a form of measurement of blood perfusion commonly used. A still further step 130 of method 100 may involve re-measuring the blood perfusion of the contrast material in the cancerous tissue and in the healthy tissue in the patient at a second examination time. This may be done using a second piece of computed tomography equipment, to obtain a second cancer/healthy perfusion ratio result. It is noted when referring to a "particular piece of computer tomography equipment" and later referring to a "second piece of computed tomography equipment", it should be clear that although the "second piece of computed tomography equipment" may very well be different from the "particular piece of computed tomography equipment" it does not necessarily have to be different from it. Likewise, a third piece of CT equipment does not necessarily have to been although it may very well be, different from the first or second piece on that patient.

Method 100 may include a further step 140 of re-measuring the blood perfusion of the contrast material in the healthy tissue phantom at the second examination time using the second piece of computed tomography equipment to obtain a second phantom perfusion result. The re-measuring for the healthy tissue and cancerous tissues in the patient and in the healthy tissue phantom may also occur at further examination times such as a third, fourth, fifth etc. examination time, as medically indicated.

Method 100 may be further extended to also include steps of (i) calculating a change between the first phantom perfusion result and the second phantom perfusion result to obtain a phantom variability; (ii) calculating a change in blood perfusion in the healthy tissue between the first examination time and the second examination time; (iii) normalizing the change in blood perfusion in the healthy tissue between the first examination time and the second examination time to reflect the phantom variability and to obtain a normalized healthy tissue perfusion reflecting healthy tissue blood perfusion conditions at the second examination time; (iv) calculating the second cancer/healthy perfusion ratio result by using the normalized healthy tissue phantom to remove contribution attributable to cardiac output and (v) calculating a relationship between the first cancer/healthy perfusion ratio result and the second cancer/healthy perfusion ratio result to obtain a true perfusion result.

This true perfusion result for the cancerous tissue may achieve a reliability that may be sufficiently high to allow a determination of drug effectiveness in tumor reduction after only a 25% reduction has been found. The number "25%" is merely a non-limiting example of a percentage significantly lower than the conventional "50% yardstick often required before finding that a drug is effective in tumor reduction for a given individual.

In the above method 100, the measurement slices over time of the first cancer/healthy perfusion ratio result may be made to coincide with the measurement slices over time of the first phantom perfusion result. Likewise, the measurement slices over time of the second cancer/healthy perfusion ratio result may be made to coincide with the measurement slices over time of the second phantom perfusion result. In this scenario, not only is it the case that the phantom measurements may be taken at the same time as the healthy and tumor measurements, but each slice of the phantom measurement may coincide with each slice of the healthy/tumor measurement.

Figure 6:
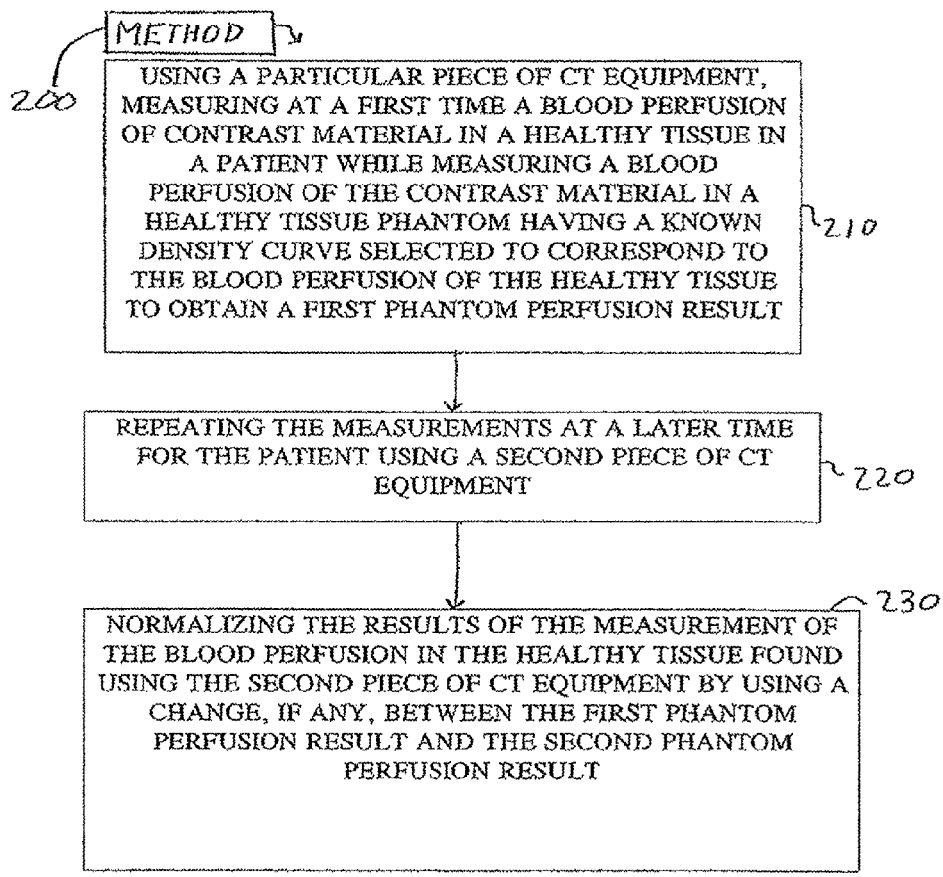
FIG. 6 is a flow chart showing a method in accordance with a further embodiment of the present invention.

As seen from FIG. 6, the present invention may also be expressed as a method 200 of controlling for variability in measurements of healthy tissue blood perfusion for computed tomography imaging. Method 200 may be comprised of a step 210 of measuring at a first time, using a particular piece of computed tomography equipment, a blood perfusion of contrast material in a healthy tissue (i.e. aorta) in a patient while measuring a blood perfusion of the contrast material in a healthy tissue phantom having a known density curve selected to correspond to the blood perfusion of the healthy tissue to obtain a first phantom perfusion result. Method 200 may further include a step 220 of repeating the measurements (of the healthy tissue as well as that of the blood vessel phantom) at a later time for that patient using a second piece of CT equipment (or a third time using a third piece of CT equipment, etc.).

Method 200 may also include a step 230 of normalizing the results of the measurement of the blood perfusion in the healthy tissue found using the second piece of CT equipment by using a change, if any, between the first phantom perfusion result and the second phantom perfusion result. This may factor out a contribution attributable to cardiac output variability.

Method 200 may also include a further step of normalizing the results by conforming a percentage change in blood perfusion in the healthy tissue from a first examination time to a second examination time to a percentage change between the first phantom perfusion result and the second phantom perfusion result. Method 200 may also be extended to include steps of (i) measuring a blood perfusion of contrast material in cancerous tissue of the patient each time the blood perfusion of contrast material in the healthy tissue may be measured; (ii) calculating a ratio of blood perfusion between the cancerous tissue and healthy tissue for the first time; (iii) calculating a ratio of blood perfusion between the cancerous tissue and healthy tissue for the later time by using the normalized results of the blood perfusion in the healthy tissue; and (iv) calculating an amount of reduction in cancerous tissue in the patient between the first time and the later time by comparing the ratio of blood perfusion for the first time with the already normalized ratio of blood perfusion for the later time.

Method 200 may allow normalizing the results to take out contribution from changes in the patient's cardiac output and from changes in the particular computed tomography machine used. It should be understood that the phrases "changes in the CT" used, "changes in CT machines", "using a different CT machine" or CT equipment and the like refer both to changes in the physical machine selected to conduct the CT examination and to changes in the algorithm used by the machine.

The following are examples of the application of the normalization procedure in accordance with one embodiment of the present invention using the apparatuses and methods 100, 200 of the present invention.

Blood perfusion results may be obtained in the form of a curve having a measurable maximum height (Pmax) and slope (rate of change from baseline to peak enhancement MaxP per second).

The following hypothetical non-exclusive examples illustrate the application of the method and apparatus of the present invention.

Example 1

A patient may be injected with a solution containing a contrast material, for example iodine, at time A for a CT examination and the flow of the contrast material through the cancerous tissue and through the healthy aorta (control tissue) of the patient is observed and imaged by a particular piece of CT equipment during the CT examination. The patient's blood perfusion as measured by the particular piece of CT equipment and is found to be X/5, where "X" represents the slope (rate of increase from baseline to MaxP or peak enhancement) of the cancerous tissue and the denominator represents the slope of the healthy tissue (i.e. aorta) of the patient. It is noted that in this example the patient's aorta does not receive the drug treatment that the patient's cancerous tissue is receiving.

The patient is asked to come back for a follow-up CT examination at time B, which in one non-limiting example might be an examination time approximately one day, one week or one month (or any other shorter or longer time interval) later than the examination time for time A. At time B the same patient's blood perfusion measurement was X/4, which indicates a 20% lower reading for the healthy tissue. Although the units that the slope is expressed in have been omitted in this example, the actual units are in fact HU per second, where "HU" stands for Hounsfield units.

In actuality, when the patient in the above example was undergoing the CT 15 examination at time A (and similarly when the patient was being examined at time B), a healthy tissue phantom in accordance with one of the embodiments of the present invention was simultaneously being examined by the same CT machine examining the patient. The blood perfusion results of this healthy tissue phantom may have been obtained at time A and at time B when the results of the patients tumor and healthy aorta were obtained. The blood perfusion results for the healthy tissue phantom were in this example found to be 5 (five) at time A and were found to be 4.6 at time B. Instead of the 20% reduction found for the patient's healthy tissue (which may be the aorta), an 8% reduction was observed. Making use of the healthy tissue phantom control reference of the present invention, it may be concluded that the changes in the patient's cardiac output appear to have accounted for 0.6 of the 1.0 reduction (from 5 to 4) of the aorta blood perfusion (i.e. 12 of the 20%). The other 0.4 reduction (i.e. 8 of the 20%) appears to have been accounted for by external factors which were experienced by both the healthy tissue (aorta) and the healthy tissue phantom control reference since the phantom control reference does not experience cardiac output fluctuations but does experience fluctuations due to use of different CT machines and/or use of different CT machine algorithms.

It is noted that at time A measurement of the healthy tissue phantom was set in advance to be "5" in the above example by designing a healthy tissue phantom to have such a slope. That slope may have been selected because the slope magnitude of "5" may be a reasonable estimate of healthy tissue blood perfusion in an adult patient. This may be based on prior CT examinations of other healthy tissue of other patients or it may be based on the results of this patient's prior examinations of their healthy aorta. In either case, the whole point of using the phantom is to have a control reference whose density curve or blood perfusion curve may be of known quantity.

Accordingly, in this simple case, the normalization of the results of the blood perfusion in the healthy tissue would involve substituting 4.6 for 4 as the arterial blood perfusion at time B in the equations. Hence, when calculating the ratio of the tumor blood perfusion to the healthy tissue blood perfusion, the denominator (healthy tissue blood perfusion) used will be the normalized denominator of healthy tissue blood perfusion. Hence, a normalized cancer/healthy perfusion ratio will be obtained for the second or later time (time B). Accordingly, when calculating the reduction of the tumor from time A to time B, cardiac output variability in the healthy tissue may not skew the results.

Example 2

After injection of contrast material in a liquid solution, the patient's blood perfusion in cancerous tissue and in healthy tissue as measured by the particular piece of CT equipment and is found to be X/6 at time A. The same patient was re-measured at a follow-up CT examination at time B. The patient's healthy tissue blood perfusion measurement at time B was found to be X/3, which represents a decline of 50% in blood perfusion of the healthy tissue between time A and time B. This means the healthy tissue was found to be (six) 6 at time A and found to be (three) 3 at time B. When the patient in example 2 was undergoing the CT examination at time A (and similarly when the patient was being examined at time B), a healthy tissue phantom in accordance with one of the embodiments of the present invention was simultaneously being examined by the same CT machine examining the patient. The blood perfusion results of this healthy tissue phantom may have been obtained at time A and at time B when the results of the patients cancerous tissue and healthy aorta were obtained. The healthy tissue phantom at time A was found to be 5 (five) and the healthy tissue phantom at time B was found to be 4 (four), which represents a decline of 20%. In example 2, the blood perfusion of the healthy tissue phantom at time A is not the same as that of the healthy tissue at time A.

In example 2 we may conclude that 20 of the 50% decline in healthy tissue results appears to have been due to using a different machine/algorithm and the remaining 30 of the 50% appears to have been due to cardiac output variability (i.e. decline) from time A to time B. Accordingly, using the method of the present invention we may normalize the healthy tissue perfusion at time B from (three) 3 units to 4.8 units. When calculating the ratio of cancerous tissue perfusion to healthy tissue perfusion at time B, we may normalize the ratio by substituting a 20% decline for the 50% decline in healthy tissue blood perfusion in the denominator of the ratio. In this case the X/3 ratio would be normalized to X/4.8.

A determination of the reduction, if any, in the tumor blood perfusion attributable to factors other than cardiac output variability and other than use of different CT equipment may be made by comparing the ratios in time A and in time B. It is understood by those skilled in the art that the normalization adjustments may be made not only to the cancer tissue/healthy tissue perfusion ratio alone but rather to the overall perfusion equation in which this ratios appears (and forms the main part of). For example, this perfusion equation may be $CBV = \Delta HU_{tissue}/\Delta HU_{artery} \cdot N$ or the other commonly used equation for calculating blood perfusion such as $$R(t) = 1/CBF \cdot \Gamma^{-1}\{[\Gamma C_{tissue}(t)]/[\Gamma AIF(t)]\}.$$

Example 3

Note that in Examples 1 and 2 the observed change in the healthy tissue phantom control reference was less than the observed change in the healthy tissue, which is what may be typical. It could happen, on the other hand, that the measured change in the healthy tissue phantom may be more than the measured change in the aorta because of a change in cardiac output in the other direction. Suppose, for example, measurement of the cancerous tissue and of the healthy tissue in the patient at time A was X/6 and at time B it was X/5.4, a decline of 10% in perfusion for the healthy tissue (e.g. aorta). When the patient in the above example was undergoing the CT examination at time A (and similarly when the patient was being examined at time B), a healthy tissue phantom in accordance with one of the embodiments of the present invention was simultaneously being examined by the same CT machine examining the patient. Suppose the healthy tissue phantom at time A was 5 (five) and at time B it was 4 (four), which represents a decline of 20%.

The decline of (twenty) 20% observed in the phantom control reference for the healthy tissue may be assumed to be caused by the use of a different machine and/or machine algorithm. In this case, the patient's cardiac blood perfusion was observed to have gone down less than that observed in the healthy tissue phantom. It may be concluded regarding the healthy tissue blood perfusion that cardiac output actually went up (ten) 10% between time A and time B and it may be further concluded that the relatively small 10% increase in cardiac output was more than counterbalanced by a larger 20% decline caused by switching to the different CT machine (or algorithm). As a result, in this example one was able to observe a decline of (ten) 10% in the healthy tissue blood perfusion during the period from time A to time B. This may be captured by the simple equation 20−10=10.

Accordingly, in this case one may choose to normalize the patient's healthy tissue blood perfusion observed at time B from 5.4 to 4.8 since the patient would have had, it is assumed, a 20% decrease in blood perfusion in the healthy tissue if there had been no cardiac output variability. Accordingly, the cancer to healthy tissue perfusion ratio may be normalized at time B from X/5.4 to X/4.8. In this case, one may adjust downward when factoring out a cardiac output increase. A determination of the reduction, if any, in the tumor blood perfusion attributable to factors other than cardiac output variability and other than use of different CT equipment may be made by comparing the ratio in time A with the normalized ratio in time B.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method of using imaging equipment to measure blood perfusion in a patient having a cancerous tissue, comprising:
   measuring a blood perfusion of contrast material in the cancerous tissue and in healthy tissue in the patient at a first examination time using a first piece of imaging equipment, to obtain a first cancer/healthy perfusion ratio result;
   measuring a blood perfusion of the contrast material in a healthy tissue phantom at the first examination time using the first piece of imaging equipment, the healthy tissue phantom having a known density curve selected to correspond to the blood perfusion of the healthy tissue to obtain a first phantom perfusion result;
   re-measuring a blood perfusion of the contrast material in the cancerous tissue and in the healthy tissue in the patient at a second examination time to obtain a second cancer/healthy perfusion ratio result using a second piece of imaging equipment; and re-measuring a blood perfusion of the contrast material in the healthy tissue phantom at the second examination time using the second piece of imaging equipment to obtain a second phantom perfusion result.

2. The method of claim 1, further including:

calculating a change between the first phantom perfusion result and the second phantom perfusion result to obtain a phantom variability;

calculating a change in blood perfusion in the healthy tissue between the first examination time and the second examination time;

normalizing the change in blood perfusion in the healthy tissue between the first examination time and the second examination time to reflect the phantom variability and to obtain a normalized healthy tissue perfusion reflecting blood perfusion conditions in the healthy tissue at the second examination time.

3. The method of claim 2, further including calculating a normalized second cancer/healthy perfusion ratio result; and calculating a relationship between the first cancer/healthy perfusion ratio result and the normalized second cancer/healthy perfusion ratio result to obtain a true perfusion result for the cancerous tissue.

4. The method of claim 1, wherein measuring the blood perfusion of the contrast material in the healthy tissue phantom involves placing the healthy tissue phantom alongside the patient in the first piece of imaging equipment during the first examination time.

5. The method of claim 4, wherein measuring the blood perfusion of the contrast material in the healthy tissue phantom involves placing the healthy tissue phantom alongside the patient in the second piece of imaging equipment during the second examination time.

6. The method of claim 1, wherein re-measuring the healthy tissue and the cancerous tissue in the patient and re-measuring the healthy phantom occurs more than once.

7. The method of claim 1, further including having the measurement slices over time of the first cancer/healthy perfusion ratio result coincide with the measurement slices over time of the first phantom perfusion result and having the measurement slices over time of the second cancer/healthy perfusion ratio result coincide with the measurement slices over time of the second phantom perfusion result.

8. The method of claim 1, further including selecting the known density curve based on a previously measured blood perfusion of the healthy tissue.

9. The method of claim 1, wherein each of the first piece of imaging equipment and the second piece of imaging equipment is computed tomography equipment.

10. The method of claim 1, wherein each of the first piece of imaging equipment and the second piece of imaging equipment is MRI imaging equipment.

11. A method of controlling for variability in measurements of healthy tissue blood perfusion during imaging, comprising:

using a first piece of imaging equipment, measuring at a first time a blood perfusion of contrast material in a healthy tissue in a patient while measuring a blood perfusion of the contrast material in a healthy tissue phantom having a known density curve selected to correspond to the blood perfusion of the healthy tissue to obtain a first phantom perfusion result;

repeating the measurements at a later time for the patient using a second piece of imaging equipment that uses a same imaging technology and an imaging technology of the first piece of imaging equipment; and normalizing the results of the measurement of the blood perfusion in the healthy tissue found using the second piece of imaging equipment by using a change, if any, between the first phantom perfusion result and the second phantom perfusion result.

12. The method of claim 11, further including normalizing the results by conforming a percentage change in blood perfusion in the healthy tissue from a first examination time to a second examination time to a percentage change between the first phantom perfusion result and the second phantom perfusion result.

13. The method of claim 11, further including normalizing the results of the blood perfusion in the healthy tissue to take out a contribution attributable to changes in the patient's cardiac output.

14. The method of claim 11, further including measuring a blood perfusion of contrast material in cancerous tissue of the patient each time the blood perfusion of contrast material in the healthy tissue is measured;

calculating a ratio of blood perfusion between the cancerous tissue and healthy tissue for the first time; and calculating a ratio of blood perfusion between the cancerous tissue and healthy tissue for the later time by using the normalized results of the blood perfusion in the healthy tissue.

15. The method of claim 14, further including calculating an amount of reduction in cancerous tissue in the patient between the first time and the later time by comparing the ratio of blood perfusion for the first time with the ratio of blood perfusion for the later time.

16. The method of claim 14, further including removing contribution from changes derived from whether the first or second piece of imaging equipment was used, by calculating a ratio of blood perfusion between the cancerous tissue and healthy tissue for the first time and by calculating a ratio of blood perfusion between the cancerous tissue and healthy tissue for the later time.

17. The method of claim 16, wherein removing contribution from changes derived from whether the first or second piece of imaging equipment was used, involves removing contribution from changes derived from whether the first or second piece of computed tomography equipment was used.

18. The method of claim 16, wherein removing contribution from changes derived from whether the first or second piece of imaging equipment was used, involves removing contribution from changes derived from whether the first or second piece of MRI imaging equipment was used.

19. The method of claim 11, wherein the healthy tissue is a healthy aorta or another large artery.

20. The method of claim 11, wherein each of the first piece of imaging equipment and the second piece of imaging equipment is computed tomography equipment.

21. The method of claim 11, wherein each of the first piece of imaging equipment and the second piece of imaging equipment is MRI imaging equipment.

22. A method of using one of MRI imaging equipment and computed tomography equipment to measure blood perfusion in a patient having a cancerous tissue, comprising:

measuring a blood perfusion of contrast material in the cancerous tissue and in healthy tissue in the patient at a first examination time using a first piece of imaging equipment, the first piece of imaging equipment comprising one of MRI imaging equipment and computed tomography equipment, to obtain a first cancer/healthy perfusion ratio result;

measuring a blood perfusion of the contrast material in a healthy tissue phantom at the first examination time using the first piece of imaging equipment, the healthy tissue phantom having a known density curve selected to correspond to the blood perfusion of the healthy tissue to obtain a first phantom perfusion result;

re-measuring a blood perfusion of the contrast material in the cancerous tissue and in the healthy tissue in the patient at a second examination time to obtain a second cancer/healthy perfusion ratio result using a second piece of imaging equipment that is computed tomography equipment if the first piece of imaging equipment used was computer tomography equipment and that is MRI imaging equipment if the first piece of imaging equipment used was MRI imaging equipment; and re-measuring a blood perfusion of the contrast material in the healthy tissue phantom at the second examination time using the second piece of imaging equipment to obtain a second phantom perfusion result.

\* \* \* \* \*